(12) United States Patent
Wershofen et al.

(10) Patent No.: US 9,701,617 B2
(45) Date of Patent: Jul. 11, 2017

(54) PROCESS FOR PRODUCING DIAMINES AND POLYAMINES OF THE DIPHENYLMETHANE SERIES

(75) Inventors: Stefan Wershofen, Mönchengladbach (DE); Heinz-Herbert Müller, Krefeld (DE); Richard Adamson, Leichlingen (DE); Fritz Pohl, Brunsbüttel (DE); Knut Sommer, Krefeld (DE)

(73) Assignee: Covestro Deutschland AG, Leverkusen (DE)

( * ) Notice: Subject to any disclaimer, the term of this patent is extended or adjusted under 35 U.S.C. 154(b) by 345 days.

(21) Appl. No.: 12/405,287

(22) Filed: Mar. 17, 2009

(65) Prior Publication Data

US 2009/0240077 A1 Sep. 24, 2009

(30) Foreign Application Priority Data

Mar. 20, 2008 (DE) .................. 10 2008 015 123

(51) Int. Cl.
*C07C 263/10* (2006.01)
*C07C 209/78* (2006.01)

(52) U.S. Cl.
CPC .......... *C07C 209/78* (2013.01); *C07C 263/10* (2013.01)

(58) Field of Classification Search
None
See application file for complete search history.

(56) References Cited

U.S. PATENT DOCUMENTS

| | | | |
|---|---|---|---|
| 4,014,914 A * | 3/1977 | Pistor et al. | 560/347 |
| 4,087,459 A * | 5/1978 | Knofel et al. | 564/331 |
| 4,792,624 A | 12/1988 | Hatfield, Jr. et al. | |
| 5,053,539 A | 10/1991 | Yano et al. | |
| 5,286,760 A | 2/1994 | Bolton et al. | |
| 5,310,769 A | 5/1994 | Konig et al. | |
| 6,433,219 B1 * | 8/2002 | Strofer et al. | 560/347 |
| 6,831,192 B2 | 12/2004 | Strofer et al. | |
| 7,041,776 B2 | 5/2006 | Koch et al. | |
| 7,230,130 B2 | 6/2007 | Strofer et al. | |
| 7,312,362 B2 * | 12/2007 | Keggenhoff et al. | 564/397 |
| 7,528,283 B2 * | 5/2009 | Pohl et al. | 564/331 |
| 2004/0092701 A1 * | 5/2004 | Koch et al. | 528/269 |
| 2006/0224018 A1 * | 10/2006 | Hagen et al. | 564/397 |
| 2007/0179316 A1 * | 8/2007 | Pohl et al. | 564/397 |
| 2007/0238901 A1 | 10/2007 | Dugal et al. | |

FOREIGN PATENT DOCUMENTS

| | | |
|---|---|---|
| DE | 238042 A1 | 8/1986 |
| DE | 295628 A5 | 11/1991 |
| DE | 19804918 A1 | 8/1999 |
| EP | 31423 B1 | 6/1984 |
| EP | 1167343 B1 | 5/2003 |
| EP | 934922 B1 | 4/2004 |
| JP | 2004026753 A | 1/2004 |

OTHER PUBLICATIONS

Sigma-Aldrich Catalog No. 242284 for reagent-grade Aniline.*
Twitchett, H.J., Chem. Soc., Rev. 3(2), 209 (1974).
Moore, W.M., Kirk-Othmer Encycl. Chem. Technol., 3rd Ed., New York, 2, 338-348 (1978).
Research Disclosure Journal, RD 510004, Kenneth Mason Publications Ltd., U.K., Oct. 2006.
Fluka Chemiekalien Katalog: "Chemica Biochemika Analytika", 1997, Sigma-Aldrich Handels GmbH, Wein, XP002532662, p. 146.

* cited by examiner

*Primary Examiner* — Karl J Puttlitz
(74) *Attorney, Agent, or Firm* — N. Denise Brown

(57) ABSTRACT

The present invention relates to a process for producing diamines and polyamines of the diphenylmethane series (MDA) by reacting aniline and formaldehyde in the presence of an acid catalyst, wherein the aniline contains in total less than 0.5 wt. %, based on the total weight of aniline, of one or more compounds which contain at least one carbonyl group or of one or more compounds that are formed by reaction of these compounds which contain at least one carbonyl group with aniline.

6 Claims, No Drawings

PROCESS FOR PRODUCING DIAMINES AND POLYAMINES OF THE DIPHENYLMETHANE SERIES

CROSS REFERENCE TO RELATED PATENT APPLICATION

The present patent application claims the right of priority under 35 U.S.C. §119 (a)-(d) of German Patent Application No. 10 2008 015 123.8, filed Mar. 20, 2008.

BACKGROUND OF THE INVENTION

The invention relates to a process for producing diamines and polyamines of the diphenylmethane series (MDA) by reacting aniline and formaldehyde in the presence of an acid catalyst, wherein the aniline used contains in total less than 0.5 wt. %, based on the weight of aniline used, of compounds which contain at least one carbonyl group or of compounds which are formed by reaction of these compounds containing at least one carbonyl group with aniline.

The compounds containing carbonyl groups and/or compounds formed therefrom by reaction with aniline may derive from the freshly used aniline, are contained in the recycled aniline or are formed as secondary products during the course of production of diamines and polyamines of the diphenylmethane series. They can optionally accumulate in the aniline recycle streams and reach contents above those in the fresh aniline.

Diamines and polyamines of the diphenylmethane series (MDA) are understood to be amines and mixtures of amines which correspond to the following structure:

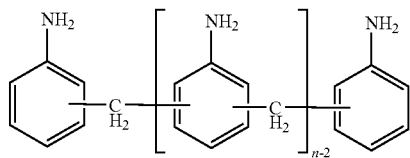

where n stands for a natural number ≥2.

For compounds and mixtures of compounds with n=2, the term monomeric MDA (MMDA) is also conventionally used, while for compounds and mixtures of compounds with n>2 the term polymeric MDA (PMDA) is also conventionally used. For the sake of simplicity, mixtures of compounds in which compounds with n=2 and n>2 occur side by side are conventionally grouped together under the term MDA (diamines and polyamines of the diphenylmethane series).

The continuous, discontinuous or semi-continuous production of diamines and polyamines of the diphenylmethane series is described in countless publications and patents (see, for example H. J. Twitchett, Chem. Soc. Rev. 3(2), 209 (1974); W. M. Moore in: Kirk-Othmer Encycl. Chem. Technol., 3$^{rd}$ Ed., New York, 2, 338-348 (1978); EP-A-31 423; EP-B-1 167 343; EP-A-1 403 242; EP 934 922 B1).

In the methods used in industry, MDA is conventionally produced by reacting aniline and formaldehyde in the presence of acid catalysts, wherein at the end of the process the acid catalyst is conventionally neutralised by addition of a base, the reaction mixture is separated into an organic and an aqueous phase and the organic phase is transferred to the subsequent processing steps, such as, for example, removal of excess aniline by distillation (see U.S. Pat. No. 5,310,769; DE-A-198 04 918; and JP-A-2004026753).

Common to all processes described in the literature for producing MDA by reacting aniline and formaldehyde in the presence of an acid catalyst is the fact that during the reaction, chromophores are formed which discolor the MDA that is produced. If these discolorations are not sufficiently reduced or removed during neutralisation of the acid catalyst and removal of the aniline used in excess in the reaction, then during the subsequent phosgenation of the MDA to form the corresponding diisocyanates and polyisocyanates of the diphenylmethane series and their subsequent processing (e.g. separation of the solvent, separation of monomeric MDI), they often lead to darkly discolored products, which in turn give rise to yellowish discolored polyurethane foams or other discolored polyurethane (PU) materials. Although the inherent color of the diisocyanates and polyisocyanates of the diphenylmethane series does not negatively influence the mechanical properties of the polyurethanes produced therefrom, light-colored products are preferred because of their good variability in the processor's production process, with regard for example to showing through thin top coats and to color design possibilities. Accordingly, there has been no shortage of attempts to reduce the discoloration of MDA and the MDI produced therefrom.

EP 1 270 544 B1 describes a process for producing MDA with minimisation of the content of undesirable secondary products by reacting aniline with formaldehyde in the presence of acid catalysts, characterised in that in a semi-continuous process aniline and optionally acid catalyst are laid out, formaldehyde and optionally acid catalyst are fed through a mixing device into a circuit in which aniline, optionally acid catalyst and optionally pre-admixed formaldehyde are circulated, and after feeding in at least 50% of the total amount of formaldehyde to be introduced, the reaction mixture is heated to a temperature of greater than 75° C. The patent claims, in particular, the minimisation of the content of N-methyl MDA, the reduction of which in MDI should, according to the teaching of this patent, lead to a crude MDI of a lighter color in a subsequent phosgenation. The improvement of the color values by reducing the content of N-methyl MDA in the MDA that is produced, by means of a special formaldehyde feed, is the basis of the following process too.

DD-A-295 628 describes for a discontinuous process the addition of formaldehyde in two steps during the condensation stage, wherein the bulk of the formaldehyde is added in the first addition at low temperature and the second addition of the remaining formaldehyde takes place at the same or a higher temperature.

EP-A-451 442 and DD-A-238 042 disclose for a continuous process the addition of formaldehyde over several process stages.

In order to improve the color values, in addition to minimising the content of N-methyl MDA, U.S. Pat. No. 5,286,760 also teaches the minimisation of the secondary components acridan and acridine. However, U.S. Pat. No. 5,286,760 modifies not the formaldehyde feed but the molecular rearrangements following the primary reaction of the formaldehyde with aniline. U.S. Pat. No. 5,286,760 describes for a continuous MDA production a partial neutralisation of the reaction mixture between the condensation stage of two molecules of aniline and one molecule of formaldehyde and the subsequent molecular rearrangement of the intermediate aminobenzylamines (i.e. ABA) that are formed, to form MDA.

U.S. Pat. No. 5,310,769 likewise intervenes primarily in the molecular rearrangements. U.S. Pat. No. 5,310,769 describes a process for producing polyamines of the diphenylmethane series by condensation of aniline with formaldehyde, subsequent reaction in the presence of an acid catalyst, neutralisation of the acid catalyst on completion of the reaction and purification of the resulting diamine/polyamine mixture by removing the excess aromatic amine by distillation, characterised in that in a preferred variant a) aniline is reacted with formaldehyde in a molar ratio of 1.5:1 to 10:1 at temperatures between 10 and 150° C.,
b) then an acid catalyst in the molar ratio of aniline to acid catalyst of 2:1 to 100:1 is added to the reaction mixture at temperatures of between 10 and 150° C., the water formed during the condensation reaction being separated off either before or after step b),
c) then the temperature of the mixture obtained in step b) is raised by at least 40° C. within 15 minutes and then heated further to the final temperature of between 105 and 200° C. and held at this temperature for 10 to 300 minutes.

U.S. Pat. No. 5,310,769 teaches that through the special temperature control during the condensation and molecular rearrangement steps, a diamine and polyamine mixture of the diphenylmethane series is obtained, the subsequent phosgenation of which provides access to especially light-colored polyurethane foams.

According to U.S. Pat. No. 4,792,624, diamine and polyamine mixtures of the diphenylmethane series, whose subsequent phosgenation leads to polyisocyanates with a greatly reduced coloration, are also obtained by application of a process characterised in that a) fast-flowing streams of aqueous aniline hydrochloride and aqueous formaldehyde in a ratio of 1.6 to 8 moles of aniline per mole of formaldehyde are intensively mixed at the inlet of a tubular-flow reactor, as a result of which a mixture containing aminobenzylamines is immediately formed,
b) the mixture produced according to a) is subsequently passed through a cooled reaction section in which the content of aminobenzylamines in the mixture rises to at least 30 wt. %,
c) the reaction mixture is removed from the cooled reaction section at the rate at which reaction mixture flows in from step a),
d) the reaction mixture from the cooled reaction section is then passed through a rearrangement section with temperatures of 60° to 200° C., causing the polyamine of the diphenylmethane series to form,
e) the reaction mixture is removed from the rearrangement section at the rate at which reaction mixture is fed into the rearrangement section,
f) the reaction mixture from the rearrangement section is supplied continuously to a neutralisation section in which the acid components are neutralised, then aniline and water are separated from the reaction mixture so that an aniline-free polyamine of the diphenylmethane series is obtained,
g) the polyamine mixture is removed from step f) at the rate at which reaction mixture is fed into the neutralisation or distillation stage, and
h) the bulk of the polyamine mixture obtained is removed into a storage tank; however, a partial stream of the polyamine mixture of 1 to 40 wt. %, relative to the combined initial weights of the amounts of aniline, aniline hydrochloride and formaldehyde fed into step a), is returned to step b) and in the ongoing process a) to h) is passed once again through steps b) to h).

According to U.S. Pat. No. 4,792,624, in order to obtain a maximum improvement in the color values it is a substantial requirement for the excess aniline used in the process to be separated from the MDA before the MDA is added to the benzylamines. According to the teaching of U.S. Pat. No. 4,792,624, the improved coloration is moreover only achieved if the recycled polyamine is added at the point where aminobenzylamines are present, and not at the stage in which aniline and formaldehyde are reacted for the first time.

EP 1 813 598 A1 teaches that the use of aniline containing less than 3 wt. %, preferably 0.001 to 3 wt. %, particularly preferably 0.01 to 1 wt. % of diamines and polyamines of the diphenylmethane series, relative to the weight of the aniline used, in the production of MDA has an advantageous effect on the color of the MDI produced therefrom by phosgenation. The diamines and polyamines of the diphenylmethane series contained in the aniline find their way into the amine used for the production of MDA, since aniline is conventionally used in excess in MDA production and the excess is returned to the process after separation of the product by distillation, for example.

Other secondary components contained in the aniline are listed for example in RD 510004 (Research Disclosure Journal, published October 2006), such as, for example, cyclohexylamine, cyclohexanol, cyclohexanone, phenol, etc., without any mention of the contents in which these secondary components are included in the aniline and the influence, if any, these secondary components have on the quality of the MDA and on the MDI obtained therefrom.

Common to many of the processes cited above and described in the literature for the production of diamines and polyamines of the diphenylmethane series by reacting aniline with formalin in the presence of acid catalysts is the fact that by modification of individual process parameters, e.g. the component dosing, the concentration of acid catalyst, the temperature control or the product composition during the molecular rearrangements, they bring about improvements in the coloration of the diamine/polyamine mixtures of the diphenylmethane series that are produced or of the isocyanates and polyurethanes produced therefrom. Nevertheless, there is still a need for new processes with still further color improvements.

Surprisingly this objective could be achieved in a process for the production of diamines and polyamines of the diphenylmethane series by reacting aniline and formaldehyde in the presence of acid catalysts, in which the aniline used contains in total less than 0.5 wt. %, preferably 0.0001 to 0.4 wt. %, more preferably 0.0001 to 0.3 wt. % and most preferably 0.0001 to 0.25 wt. %, based on the weight of aniline used, of certain types of compounds as described herein.

SUMMARY OF THE INVENTION

The present invention relates to a process for producing diamines and polyamines of the diphenylmethane series. This process comprises reacting aniline and formaldehyde in the presence of an acid catalyst, wherein the aniline used contains in total less than 0.5 wt. %, preferably 0.0001 to 0.4 wt. %, more preferably 0.0001 to 0.3 wt. % and most preferably 0.0001 to 0.25 wt. %, based on the total weight of aniline used, of one or more compounds which contain at least one carbonyl group or of one or more compounds which are formed by reaction of the compounds which contain at least one carbonyl group with aniline.

DETAILED DESCRIPTION OF THE INVENTION

The amounts specified above are understood to be the total contents of the individual compounds containing carbonyl groups and the compounds formed from one or more compounds containing carbonyl group by reaction with aniline. Individual compounds containing carbonyl groups or individual compounds formed therefrom by reaction with aniline can preferably have a content of less than 0.4 wt. %, more preferably 0.0001 to 0.3 wt. %, most preferably 0.0001 to 0.25 wt. % and most particularly preferably 0.0001 to 0.2 wt. %, based on the weight of aniline used.

The compounds containing at least one carbonyl group and the compounds which are formed by the reaction of these compounds containing at least one carbonyl group with aniline may derive from the freshly used aniline, may be contained in the recycled aniline or may be formed as secondary products during the course of production of diamines and polyamines of the diphenylmethane series. These compounds can optionally accumulate in the aniline recycle streams and reach contents above those in the fresh aniline.

In addition to the compounds containing at least one carbonyl group and the compounds that can form by the reaction of these compounds containing at least one carbonyl group with aniline, the aniline generally also contains further impurities which can negatively influence the color of the MDI. Their influence on the color of the MDI after phosgenation of the MDA is not so pronounced, however. The content of these impurities in the aniline should nevertheless be kept as low as possible. These impurities generally contained in the aniline include inter alia the following compounds or classes of compounds, the list being provided by way of example rather than by way of limitation: optionally unsaturated and/or substituted (cyclo)aliphatic hydrocarbons such as cyclohexane, cyclohexene and methylcyclohexane, optionally substituted aromatic hydrocarbons such as benzene, toluene, ethylbenzene and the isomeric xylenes, nitro aromatics such as nitrobenzene, the isomeric dinitrobenzenes, the isomeric nitrotoluenes and the isomeric dinitrotoluenes, optionally unsaturated and/or substituted (cyclo)aliphatic alcohols such as cyclohexanol, optionally substituted phenols such as phenol and the isomeric cresols, optionally unsaturated and/or substituted (cyclo)aliphatic primary, secondary or tertiary amines such as cyclohexylamine, N,N-dicyclohexylamine and N-methylcyclohexylamine, aromatic primary, secondary or tertiary monoamines, diamines and polyamines optionally substituted at the aromatic or at the nitrogen, such as o-toluidine, m-toluidine, p-toluidine, o-phenylenediamine, m-phenylenediamine, p-phenylenediamine, N-methylaniline, N-ethylaniline, N,N-diethylaniline, the isomeric N-ethyltoluidines, the isomeric N,N-diethyltoluidines, N-cyclohexylaniline, diphenylamine, o-aminophenol, m-aminophenol, p-aminophenol and o-aminodiphenyl, diamines and polyamines of the diphenylmethane series (MDA), nitrogen-containing heteroaromatic hydrocarbons or structures derived therefrom such as phenazine, acridine, acridan, pyridine and optionally substituted and/or optionally (partially) saturated quinazolines such as N-phenyldihydroquinazoline and N-phenyltetrahydroquinazoline.

While the amino group-containing impurities in aniline are already known in the prior art and in many cases have been identified as a possible cause of quality problems (e.g. for elevated color values in the diamine/polyamine mixtures of the diphenylmethane series that are produced or the isocyanates and polyurethanes produced therefrom), some compounds/classes of compounds contained in aniline should be regarded as largely inert. They scarcely merit consideration as causes of significant quality problems, including elevated color values, in the diamine/polyamine mixtures of the diphenylmethane series that are produced or in the isocyanates and polyurethanes produced therefrom.

This applies, for example, to optionally unsaturated and/or substituted (cyclo)aliphatic alcohols such as cyclohexanol, whose presence in aniline does not lead to elevated color values in the diamine/polyamine mixtures of the diphenylmethane series that are formed or in the isocyanates and polyurethanes produced therefrom.

It is therefore completely surprising that the class of the compounds containing carbonyl groups, and in particular, the class of compounds of the optionally unsaturated and/or substituted (cyclo)aliphatic ketones, such as e.g. cyclohexanone, and the products formed therefrom by reaction with aniline such as, for example, Schiff bases such as N-phenylcyclohexylimine, which are structurally similar to the largely inert alcohols, give rise to marked quality problems and in particular elevated color values in the diamine/polyamine mixtures of the diphenylmethane series that are produced and in the isocyanates (diisocyanates and polyisocyanates of the diphenylmethane series) and polyurethanes produced therefrom.

In accordance with the present invention, the use of aniline containing in total less than 0.5 wt. %, preferably 0.0001 to 0.4 wt. %, more preferably 0.0001 to 0.3 wt. % and most preferably 0.0001 to 0.25 wt. %, based on the total weight of aniline used, of compounds containing at least one carbonyl group or of compounds formed by the reaction of these compounds containing at least one carbonyl group with aniline, is especially important because the reaction of aniline with formaldehyde in the presence of acid catalysts to adjust the desired content of diamines and to maintain the ease of use of the reaction mixtures is always performed with an excess of aniline. This excess aniline has to be separated off during processing of the diamine/polyamine mixtures of the diphenylmethane series and returned to the reaction stages of the process in order to maintain the external mass balance. Aniline consumed during the MDA synthesis is supplemented in the form of fresh aniline. The process according to the invention for producing diamines and polyamines of the diphenylmethane series by reacting aniline and formaldehyde in the presence of an acid catalyst, preferably hydrochloric acid, is therefore preferably performed in such a way that the aniline is used in a stoichiometric excess, the excess aniline is separated off after the reaction and at least part of the excess aniline is returned to the reaction of aniline and formaldehyde.

The separation of the excess aniline from the reaction mixture obtained during reaction of aniline and formaldehyde is conventionally performed by distillation, wherein water still adhering to the polyamine mixture is likewise separated off.

In order to purify the waste water that accumulates during the reaction of aniline with formalin (formaldehyde) in the presence of acid catalysts with subsequent neutralisation and separation and processing of the organic phase, the waste water, as is conventionally the case according to the prior art (as disclosed in JP 2004026753), can optionally be extracted with an additionally used hydrophobic solvent. Alternatively, the waste water can be purified by mixing it with the condensates from the aniline separation that do not undergo further processing or with fresh aniline, with subsequent phase separation. The organic phase obtained in this way can then be returned to the synthesis stages of the process as described above.

In one embodiment of the present invention, the process for producing diamines and polyamines of the diphenylmethane series, comprises a) reacting aniline and formaldehyde in the presence of an acid catalyst to form a reaction mixture containing diamines and polyamines, wherein the aniline used contains in total less than 0.5 wt. %, preferably 0.0001 to 0.4 wt. %, more preferably 0.0001 to 0.3 wt. % and most preferably 0.0001 to 0.25 wt. %, based on the total weight of aniline used, of one or more compounds which contain at least one carbonyl group or of one or more compounds which are formed by reaction of these compounds containing at least one carbonyl group with aniline,
b) neutralising the reaction mixture containing diamines and polyamines,
c) separating the neutralised reaction mixture containing diamines and polyamines into an organic phase containing diamines and polyamines and an aqueous phase,
d) optionally, washing the organic phase with water,
e) removing the excess aniline from the organic phase by distillation,
f) combining, in whole or in part, the waste water and condensates which accumulate in steps a) to e), wherein at least the waste water and condensates obtained in steps c) and e) are combined at least in part, and wherein a mixture containing water, diamines and polyamines, aniline and salts of the catalyst used in step a) is obtained, and
g) phase separating the mixture obtained in step f), wherein an aniline containing water together with diamines and polyamines is obtained, and
h) returning the aniline obtained in the phase separation, at least in part, to the reaction in step a).

The aniline containing water together with diamines and polyamines obtained in the phase separation in step g) is preferably additionally fed in part to one of steps b) to e).

The extracted waste water obtained in step g) preferably undergoes extraction with aniline, preferably fresh aniline. It is also preferred that the extracts obtained in this way are preferably added to the mixture obtained in step f).

The described use of aniline containing in total less than 0.5 wt. %, preferably 0.0001 to 0.4 wt. %, more preferably 0.0001 to 0.3 wt. % and most preferably 0.0001 to 0.25 wt. %, based on the total weight of aniline used, of one or more compounds which contain at least one carbonyl group or of one or more compounds which are formed by reaction of these compounds containing at least one carbonyl group with aniline, to produce diamine/polyamine mixtures having low color values can take place in all known processes for producing MDA from aniline and formaldehyde in the presence of acid catalysts. Hydrochloric acid is preferably used as the acid catalyst, however. The only substantial requirement is that the specified limits of the content of the aforementioned impurities in the aniline used are observed in the equipment for the single-stage or multi-stage reaction of aniline with formaldehyde and that local overconcentrations are avoided. Preferably, however, a homogeneous catalyst, more preferably hydrochloric acid, is used as the acid catalyst. If heterogeneous catalysts are used, the proceeding reaction mechanisms are overlaid by other influences, such as transport phenomena for example.

The aniline used in step a) is preferably produced by combining at least part of the aniline obtained in step g) containing diamines and polyamines with aniline from other sources, preferably fresh aniline. The substantial requirement here is that the aniline used contains in total less than 0.5 wt. %, preferably 0.0001 to 0.4 wt. %, more preferably 0.0001 to 0.3 wt. % and most preferably 0.0001 to 0.25 wt. %, based on the total weight of aniline used, of one or more compounds which contain at least one carbonyl group or of one or more compounds which are formed by reaction of these compounds containing at least one carbonyl group with aniline. Any excess amounts of the aniline obtained in step g) which contain water together with diamines and polyamines are preferably sent to the neutralisation and/or processing stages for the diamine/polyamine mixtures (i.e. steps b) to e) as described above).

This procedure ensures the low content of diamines and polyamines in the aniline used in the reaction in step a) that is necessary for the production of light-colored diamine/polyamine mixtures of the diphenylmethane series or isocyanates and polyurethanes produced therefrom. This procedure also advantageously minimises the effort involved in processing the polyamine mixtures in step e) and the energy input needed for processing the extracts obtained in step g). This advantage is derived from the fact that the production of diamines and polyamines of the diphenylmethane series is carried out in industry on such a large scale that even minor economic improvements to such important industrial processes are of great economic interest.

In step a) the aniline containing in total less than 0.5 wt. %, preferably 0.0001 to 0.4 wt. %, more preferably 0.0001 to 0.3 wt. % and most preferably 0.0001 to 0.25 wt. %, based on the total weight of aniline used, of one or more compounds which contain at least one carbonyl group or of one or more compounds which are formed by reaction of these compounds containing at least one carbonyl group with aniline, is reacted first with formaldehyde in a molar ratio of preferably 1.6:1 to 10:1, more preferably 1.6:1 to 4.0:1, and at a temperature of preferably between 10 and 150° C., more preferably between 75 and 110° C.

Then an acid catalyst is preferably added to the reaction mixture in a molar ratio to of aniline to acid catalyst of preferably 2:1 to 100:1 (corresponding to a degree of protonation of aniline of 50 to 1%), more preferably 4:1 to 20:1, at a temperature of preferably 10 to 150° C., more preferably 35 to 75° C. Hydrochloric acid is preferably used as the acid catalyst.

The water formed during condensation of the formaldehyde with the aniline and optionally introduced with the formaldehyde is preferably separated in whole or in part prior to the catalyst addition (e.g. by phase separation) and/or afterwards (e.g. by evaporative cooling and removal of the condensates obtained).

The reaction mixture is then preferably heated to temperatures of between 100 and 180° C., more preferably between 130 and 160° C., and after reaching the final temperature is held at this temperature for 5 to 300 minutes.

In step b) the reaction mixture containing MDA is then optionally neutralised by adding water and/or aniline. Neutralisation is preferably performed with sodium hydroxide solution.

In step c) the neutralised reaction mixture containing MDA is then separated into an organic phase containing MDA and an aqueous phase. This can be supported by the addition of aniline and/or water. If the phase separation is supported by the addition of aniline and/or water, they are preferably added with intensive mixing during neutralisation. The mixing can take place in mixing sections with static mixers, in stirred-tank reactors or series of stirred-tank reactors or in a combination of mixing sections and stirred-tank reactors. The neutralised reaction mixture, which has been diluted by the addition of aniline and/or water, is then preferably transferred to an apparatus which by virtue of its configuration and/or internal fittings is particularly suitable for separating the mixture into an organic phase containing MDA and an aqueous phase. Vessels or tanks having as internal fittings sets of plates supporting coalescence of the two phases are preferably used.

In step d) the organic phase containing MDA is optionally washed with water, preferably at temperatures of between 50 and 150° C., more preferably between 80 and 110° C., in a ratio of water to organic phase of 0.05 to 2:1.

After optional washing in step d), the organic phase obtained in step c) is then freed from aniline by distillation in step e), resulting in a purified MDA and a condensate containing aniline and water.

The waste waters obtained in steps a) to e), such as the aqueous phase from step c), the washing water from step d), and the condensate from step e), and optionally other process water such as, for example, further condensed vapors or aqueous phases obtained in step a), are then combined in part or in whole in step f). At least part, and preferably at least 50% by weight, of the waste water and condensates obtained at least in steps c) and e) are combined here. A mixture is obtained in this way which preferably contains water and 0.001 to 5 wt. % of MDA, 0.5 to 60 wt. % of aniline and 1 to 25 wt. % of salts of the acid catalyst used in step a), based (in each case) on the total weight of the mixture.

The mixture obtained in step f) then undergoes a phase separation in step g), preferably at a temperature of between 30 and 120° C., more preferably between 70 and 110° C., to produce an aniline containing diamines and polyamines.

In a further step, the waste water obtained in step g) can optionally be extracted in a further step comprising an extraction with aniline, preferably with fresh aniline, preferably at a temperature of between 30 and 120° C., more preferably between 70 and 110° C., with aniline in a ratio by weight of aniline to waste water of preferably 0.05 to 1:1, more preferably 0.1 to 0.3:1, with the extracts advantageously being supplied to the mixture prepared in step f). The extraction is preferably performed in several stages and in countercurrent. Aniline is preferably used as the sole extracting agent.

The extraction with fresh aniline is advantageously supported by the phase separation performed in step f) (which involves an extraction) and the extraction performed in step g) of the waste water with the condensates from the aniline removal by distillation performed in step e). Very small amounts of fresh aniline are thus required for extraction. Since the condensates are free from phenol, the phenol loading in the extracted waste water is low.

Removal of the aniline from the extracted waste water by distillation is advantageous. Aniline forms a low-boiling azeotrope with water, so the removal of aniline by distillation can be performed at (or optionally only slightly) reduced pressure, which is simple to set up and to use in industry, at temperatures of below 100° C., such that even the waste heat can advantageously be used as energy in the recovery of aniline by distillation.

The condensates obtained from the extracted waste water during removal of aniline by distillation have a high water content. The condensates can therefore advantageously be used in whole or in part as dilution water in the neutralisation in step b) and as washing water in step d), more preferably first as washing water in step d) and then as dilution water in the neutralisation in step b). In this way, a large amount of washing water can be used without increasing the amount of waste water produced by the process.

If during the removal of aniline by distillation from the extracted waste water the vapors are condensed, a fraction containing high concentrations of methanol and other low-boiling components can be produced. Not only does this advantageously reduce the methanol level in the process stages but also this fraction can advantageously be used as a fuel substitute.

Finally in step h) the aniline obtained in the phase separation in step g), containing water together with diamines and polyamines, is returned in part or in full to step a). The recycled aniline is preferably used in the reaction in step a) with no further processing. A further part can optionally be used in one of process steps b) to e).

The process according to the invention is characterised by the fact that the aniline-containing streams arising from the extractive processing of its waste water and condensates are particularly easy to handle. Furthermore, the polyamines produced by the process according to the invention have low chromophore contents and can advantageously be converted into only slightly colored isocyanates or light-colored polyurethane products. Phosgenation of the polyamines and isolation of the polyisocyanates obtained and their conversion into polyurethane products can be performed by known industrial processes.

New and substantial to the process according to the invention is the fact that in the reaction of aniline and formaldehyde, an aniline is used that contains in total less than 0.5 wt. %, preferably 0.0001 to 0.4 wt. %, more preferably 0.0001 to 0.3 wt. % and most preferably 0.0001 to 0.25 wt. %, based on the total weight of aniline used, of one or more compounds which contain at least one carbonyl group or of one or more compounds which are formed by reaction of these compounds containing at least one carbonyl group with aniline. Owing to the low content in the aniline used of impurities containing carbonyl groups and of compounds formed by reaction of these compounds containing at least one carbonyl group with aniline, improved color values are obtained in the diamines and polyamines of the diphenylmethane series and in the diisocyanates and polyisocyanates of the diphenylmethane series and the polyurethanes produced therefrom.

The process according to the invention is preferably performed in such a way that the extraction with aniline takes place after phase separation of the neutralised reaction mixture containing MDA, wherein only extraction of the aqueous phase is carried out with aniline and the aniline-containing condensates obtained in step e) from the removal of aniline by distillation are primarily used as extracting agents in step g). That is because the phase separation in step g) takes place with almost simultaneous extraction of the aqueous phase due to the aniline contained in the highly aniline-containing condensates (organic phase). The reaction mixture still containing the two phases or the organic phase obtained after phase separation is not extracted with aniline by the process according to the invention. By separating off the waste water and using the condensates, the use and processing of an additional hydrophobic solvent can be avoided, in contrast to the prior art, and only extremely small amounts of fresh aniline, if any at all, are needed for processing the waste water.

The coloration of the diisocyanates and polyisocyanates can be characterised by two absorption maxima in the visible UV range at 430 and 520 nm. With appropriate experience, these values can be used to predict the coloration of the polyurethane products produced from the diisocyanates and polyisocyanates of the diphenylmethane series. The value at 430 nm corresponds to a yellow-brown coloration, that at 520 nm to a grey coloration. Lower absorption values for the diisocyanates and polyisocyanates correspond to lesser or lighter colorations in the polyurethane products produced from these diisocyanates and polyisocyanates of the diphenylmethane series.

The processes according to the invention are illustrated in more detail by reference to the examples below:

EXAMPLES

General Procedure for the Production of MDA

Starting Materials:
Aniline
Formaldehyde, 32 wt. % solution in water (also known as formalin)
30 wt. % aqueous hydrochloric acid
50 wt. % sodium hydroxide solution
Distilled water
General Process:
134 g of a 32 wt. % aqueous formaldehyde solution were added dropwise within 20 minutes, while stirring at 80° C., to 279 g of pure aniline (i.e. aniline containing no measurable amounts of compounds which contain at least one carbonyl group or of compounds formed by reaction of these compounds containing at least one carbonyl group with aniline), to which cyclohexanol, cyclohexanone or N-phenylcyclohexylimine was optionally added (see Table 1). Following the addition, stirring was continued for an additional 5 minutes and a phase separation was performed at 80° C. 91 g of a 30 wt. % aqueous hydrochloric acid were then added to the organic phase, the aminal, within 30 minutes while stirring at 35° C. After stirring for 30 minutes at 35° C., the reaction mixture was heated to 60° C. and stirring was continued for a further 30 minutes at 60° C. The reaction temperature was then raised to 104° C. The reaction mixture was then stirred for a further 10 hours at this temperature to complete the reaction.

72 g of a 50 wt. % sodium hydroxide solution and 100 g of water were added to the acid reaction mixture produced in the manner described above, in a stirred-tank reactor at a temperature of 95 to 100° C. while stirring. The two-phase mixture that forms was stirred for a further 15 minutes or so at 95 to 100° C. After separating off the aqueous phase, the organic phase was washed twice with 300 ml of boiling distilled water by heating to reflux temperature for approx. 5 minutes with stirring after adding the water and then separating off the aqueous phase.

After the second washing cycle, the organic phase was transferred to a distillation apparatus. Water and aniline were distilled off in the water jet vacuum (approx. 20 mbar). Distillation was stopped when the bottom temperature reaches approx. 280° C. and binuclear MDA begins to distil. The bottoms (product) were cooled, and after venting the distillation apparatus with nitrogen, were transferred to a storage vessel and stored under nitrogen. The MDA obtained had a content of 2-ring MDA (i.e. MMDA, sum of 4,4'-MDA, s,4'-MDA and 2,2'-MDA) of approx. 63%.

General Procedure for Phosgenation

Starting Materials:
MDA obtained by acid-catalysed condensation of aniline with formaldehyde according to the general procedure above
Anhydrous chlorobenzene
Phosgene
50 g of the MDA prepared according to the above process was dissolved in 255 ml of chlorobenzene, heated to 55° C. and poured into a solution of 105 g of phosgene in 310 ml of chlorobenzene at a temperature of 0° C. within 10 s with intensive stirring. The suspension was heated to 100° C. within 45 minutes by passing through phosgene and then heated to reflux temperature for 10 minutes. After a further 10 minutes at this temperature, the solvent was distilled off under reduced pressure down to a bottom temperature of 100° C. The crude isocyanate was then heated in a distillation apparatus at a pressure of 4 to 6 mbar by means of a hot air blower until the first product starts distilling and then cooled to room temperature within 5 to 10 minutes. Of the isocyanate obtained in this way, 1.0 g was dissolved in chlorobenzene and diluted with chlorobenzene to 50 ml. The absorption of the solution obtained in this way was determined at the two wavelengths of 430 nm and 520 nm. A Dr. Lange LICO 300 photometer was used as the measuring instrument. The results are summarized in Table 1.

TABLE 1

|  | Addition | [wt. %] | E 430 | E 520 |
| --- | --- | --- | --- | --- |
| Standard | — | — | 0.154 | 0.024 |
| Comparative example | Cyclohexanol | 0.5 | 0.134 | 0.021 |
| Example 1 | Cyclohexanone | 0.05 | 0.189 | 0.034 |
| Example 2 | Cyclohexanone | 0.1 | 0.221 | 0.042 |
| Example 3 | Cyclohexanone | 0.5 | 1.016 | 0.047 |
| Example 4 | Cyclohexanone | 1.0 | 1.676 | 0.074 |
| Example 5 | Cyclohexanone | 2.0 | 2.624 | 0.135 |
| Example 6 | N-Phenylcyclohexylimine | 0.05 | 0.172 | 0.028 |
| Example 7 | N-Phenylcyclohexylimine | 0.5 | 0.629 | 0.026 |
| Example 8 | N-Phenylcyclohexylimine | 1.0 | 1.106 | 0.042 |
| Example 9 | N-Phenylcyclohexylimine | 2.0 | 1.947 | 0.083 |

Result:

The comparison of the standard and Examples 1, 2 and 6 according to the invention with the other examples which are not representative of the invention (i.e. Examples 3-5 and 7-9) shows that at elevated concentrations, cyclohexanone and N-phenylcyclohexylimine, which forms from the reaction of cyclohexanone with aniline, are highly coloring compounds. This is evidenced by the dramatically increased absorption values at 430 and 520 nm. At the same time, a comparison of the comparative example (Comparative Example 1) with the corresponding standard shows that although cyclohexanol is structurally very similar to cyclohexanone, cyclohexanol has virtually no discoloring effect. For that reason, the finding that compounds which contain at least one carbonyl group or which are formed by reaction of these compounds containing at least one carbonyl group with aniline, such as cyclohexanone and N-phenylcyclohexylimine, which was formed therefrom by reaction with aniline, have a pronounced negative effect on the product color, can be considered to be most surprising.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. A process for producing diamines and polyamines of the diphenylmethane series, comprising
   a) reacting aniline and formaldehyde in the presence of an acid catalyst to form a reaction mixture containing diamines and polyamines, wherein the aniline used contains in total from 0.0001 to 0.25 wt. %, based on the total weight of aniline, of one or more compounds which contain at least one carbonyl group or of one or more compounds which are formed by reaction of one or more compounds which contain at least one carbonyl group with aniline;

b) neutralizing the reaction mixture containing diamines and polyamines of the diphenylmethane series, c) separating the neutralized reaction mixture containing diamines and polyamines of the diphenylmethane series into an organic phase containing diamines and polyamines of the diphenylmethane series and an aqueous phase;

d) optionally, washing the organic phase with water;

e) removing excess aniline from the organic phase by distillation;

f) combining; in whole or in part, waste water and condensates which accumulate in steps a) to e), wherein at least the waste water and condensates obtained in steps c) and e) are combined at least in part, and wherein a mixture containing water, diamines and polyamines of the diphenylmethane series, aniline and salts of the catalyst used in step a) is obtained;

g) phase separating the mixture obtained in step f), wherein an aniline containing water together with diamines and polyamines of the diphenylmethane series is obtained;

and h) returning the aniline obtained in the phase separation, at least in part, to the reaction in step a), wherein the aniline used in step a) is produced by combining at least part of the aniline obtained in step g) containing diamines and polyamines with fresh aniline.

2. The process of claim 1; wherein said aniline contains one or more compounds which contain at least one carbonyl group, with said compounds being selected from the group consisting of one or more optionally unsaturated (cyclo) aliphatic ketones and one or more substituted (cyclo)aliphatic ketones.

3. The process of claim 2, wherein said (cyclo)aliphatic ketone comprises cyclohexanone.

4. The process of claim 1, wherein said aniline contains one or more Schiff bases which are formed by reaction of one or more compounds which contain at least one carbonyl group with aniline.

5. The process of claim 4, wherein the Schiff base is N-phenylcyclohexylimine.

6. A process for producing diisocyanates and polyisocyanates of the diphenylmethane series, comprising reacting diamines and polyamines of the diphenylmethane series produced by the process of claim 1 with phosgene, thus forming the corresponding diisocyanates and polyisocyanates of the diphenylmethane series.

* * * * *